(12) United States Patent
Radzik

(10) Patent No.: US 8,602,215 B2
(45) Date of Patent: Dec. 10, 2013

(54) METHODS FOR REDUCING THE RISK OF AN ADVERSE DRONEDARONE/BETA-BLOCKERS INTERACTION IN A PATIENT SUFFERING FROM ATRIAL FIBRILLATION

(75) Inventor: Davide Radzik, Paris (FR)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 13/172,984

(22) Filed: Jun. 30, 2011

(65) Prior Publication Data

US 2012/0000806 A1    Jan. 5, 2012

Related U.S. Application Data

(60) Provisional application No. 61/360,121, filed on Jun. 30, 2010.

(51) Int. Cl.
B65D 90/48 (2006.01)
A61K 31/343 (2006.01)
A61P 9/00 (2006.01)

(52) U.S. Cl.
USPC ........................ 206/459.5; 514/469

(58) Field of Classification Search
USPC ........................ 206/459.5; 514/469
See application file for complete search history.

(56) References Cited

U.S. PATENT DOCUMENTS

| | | | |
|---|---|---|---|
| 4,868,179 A | 9/1989 | Cohn | |
| 4,988,513 A | 1/1991 | Griffity | |
| 5,223,510 A | 6/1993 | Gubin et al. | |
| 5,985,915 A | 11/1999 | Frangin et al. | |
| 6,218,414 B1 | 4/2001 | Nisato | |
| 6,297,287 B1 | 10/2001 | Bergeron | |
| 6,828,448 B2 | 12/2004 | Fino et al. | |
| 6,846,936 B2 | 1/2005 | Biard | |
| 6,939,865 B2 | 9/2005 | Bourriague-Seve et al. | |
| 6,951,844 B2 | 10/2005 | Hangeland | |
| 7,323,493 B1 | 1/2008 | Abramovici et al. | |
| 2001/0012900 A1 | 8/2001 | Schouteeten et al. | |
| 2002/0150622 A1 | 10/2002 | Philbrook et al. | |
| 2003/0073127 A1 | 4/2003 | Ji et al. | |
| 2003/0113330 A1 | 6/2003 | Uhal | |
| 2003/0229007 A1 | 12/2003 | Levi et al. | |
| 2004/0034220 A1 | 2/2004 | Magerlein | |
| 2005/0004194 A1 | 1/2005 | Graves | |
| 2005/0027331 A1 | 2/2005 | Bardy | |
| 2005/0070552 A1 | 3/2005 | Fedida et al. | |
| 2005/0182105 A1 | 8/2005 | Nirschl et al. | |
| 2005/0187267 A1 | 8/2005 | Hamann et al. | |
| 2005/0250783 A1 | 11/2005 | Johnson et al. | |
| 2006/0093673 A1 | 5/2006 | Coury et al. | |
| 2006/0135536 A9 | 6/2006 | Fedida et al. | |
| 2007/0243257 A1 | 10/2007 | Bedos et al. | |
| 2007/0248564 A1 | 10/2007 | Wilson et al. | |
| 2009/0076137 A1 | 3/2009 | Czarnik | |
| 2010/0016423 A1 | 1/2010 | Claudel et al. | |
| 2010/0048694 A1 | 2/2010 | Radzik | |
| 2011/0124724 A1 | 5/2011 | Gaudin et al. | |
| 2011/0136899 A1 | 6/2011 | Radzik | |
| 2011/0166220 A1 | 7/2011 | Gaudin et al. | |
| 2011/0166221 A1 | 7/2011 | Gaudin et al. | |
| 2011/0213027 A1 | 9/2011 | Radzik et al. | |
| 2011/0224293 A1 | 9/2011 | Radzik et al. | |
| 2011/0230552 A1 | 9/2011 | Gaudin et al. | |
| 2011/0297563 A1 | 12/2011 | Scarazzini | |
| 2012/0005128 A1 | 1/2012 | Gaud et al. | |

FOREIGN PATENT DOCUMENTS

| | | |
|---|---|---|
| CN | 101152154 A | 4/2008 |
| CN | 101153012 A | 4/2008 |
| EP | 0338746 | 4/1989 |
| EP | 0 471 609 B1 | 11/1996 |
| EP | 0 752 249 A2 | 1/1997 |
| EP | 0 796 617 A1 | 9/1997 |
| EP | 1 343 473 B1 | 9/2003 |
| EP | 1782829 | 5/2007 |
| FR | 2 817 865 A1 | 6/2002 |
| FR | 2 930 148 | 10/2009 |
| FR | 2930150 | 10/2009 |
| JP | 2004339218 A | 12/2004 |
| WO | WO 97/34597 A1 | 9/1997 |
| WO | WO 98/40067 A1 | 9/1998 |
| WO | WO 98/58643 A1 | 12/1998 |
| WO | WO 99/64050 A1 | 12/1999 |
| WO | WO 00/27380 A2 | 5/2000 |
| WO | WO 02/15891 A2 | 2/2002 |
| WO | WO 02/47660 A1 | 6/2002 |
| WO | WO 02/48132 A1 | 6/2002 |

(Continued)

OTHER PUBLICATIONS

Aselaki, et al., Comparative Antiarrhythmic Efficacy of Amiodarone and Dronedarone During Acute Myocardial Infarction in Rats, Eur J Pharmacol (2007) 564, pp. 150-157.

Aimond, et al., Cellular and In Vivo Electrophysiological Effects of Dronedarone in Normal and Postmyocardial infarcted Rats, JPET, (2000), vol. 292 pp. 415-424.

Altomare, et al., Effects of dronedarone on Acetylcholine-activated current in rabbit SAN cells, Br. J. Pharmacol, (2000), vol. 130, pp. 1315-1320.

Anderson, et al., Oral Flecainide Acetate for the Treatment of Ventricular Arrhythmias, The New England Journal of Medicine, vol. 305, No. 9, (1981), pp. 473-477.

(Continued)

*Primary Examiner* — Savitha Rao
(74) *Attorney, Agent, or Firm* — Kelly L. Bender

(57) ABSTRACT

The disclosure relates to a method for managing the risk of dronedarone/beta-blockers interaction by using dronedarone or pharmaceutically acceptable salts thereof in patients with paroxysmal or persistent atrial fibrillation (AF) or atrial flutter (AFL), with a recent episode of AF/AFL and associated cardiovascular risk factors, who are in sinus rhythm or who will be cardioverted to reduce the risk of cardiovascular hospitalization, said patients also expecting to receive a beta-blockers treatment, by performing the following steps:
   a—initiate beta-blockers treatment at a low dose;
   b—performing a electrocardiogram (ECG) verification of good tolerability;
   c—increase of beta-blockers dose only if results in step b) are satisfying.

16 Claims, No Drawings

(56) References Cited

FOREIGN PATENT DOCUMENTS

| | | |
|---|---|---|
| WO | WO 03/040120 A1 | 5/2003 |
| WO | WO 2005/018635 A2 | 3/2005 |
| WO | WO 2005/048979 A2 | 6/2005 |
| WO | WO 2005/066149 A1 | 7/2005 |
| WO | WO 2005/105096 A2 | 11/2005 |
| WO | WO 2006/032762 A2 | 3/2006 |
| WO | WO 2007/009462 A2 | 1/2007 |
| WO | WO 2007/039263 A2 | 4/2007 |
| WO | WO 2007/140989 A2 | 12/2007 |
| WO | WO 2008/044261 A1 | 4/2008 |
| WO | WO 2008/139057 A2 | 11/2008 |
| WO | WO 2008/141189 A1 | 11/2008 |
| WO | WO 2008/152217 A2 | 12/2008 |
| WO | WO 2009/044143 A2 | 4/2009 |
| WO | WO 2009/133310 A2 | 11/2009 |
| WO | WO 2009/133470 A2 | 11/2009 |
| WO | WO 2009/144550 | 12/2009 |
| WO | WO 2009/150534 A1 | 12/2009 |
| WO | WO 2009/150535 A1 | 12/2009 |
| WO | WO 2010/015939 A1 | 2/2010 |
| WO | WO 2011/141872 A1 | 11/2011 |

OTHER PUBLICATIONS

Andreev et al, A rise in plasma creatinine that is not a sign of renal failure: which drugs can be responsible?, J. of Internal Medicine, (1999), vol. 246, pp. 247-252.
Anonymous, Dronedarone: dronedarone, SR33589, SR33589B, Drugs R D (2007), vol. 3, No. 3, pp. 171-175.
Arlet, et al., [Correspondence Related to Singh et al, NEJM (2007) 357 pp. 987-999] Dronedarone in Atrial Fibrillation, NEJM 2007 (357) 23 pp. 2403-2405.
Aronow, Management of atrial fibrillation in the elderly, Minerva Med. (2009) 100 (1) pp. 3-24.
Bajpai, et al., Treatment of atrial fibrillation, Br. Med. Bulletin (2008) 88 (1) pp. 75-94.
Baker, New Drugs Approved by the FDA New Dosage Forms and indications Agents Pending FDA Approval Significant Labeling Changes: Hospital Pharmacey, vol. 41, No. 11, (2006), pp. 1086-1089.
Barthelemy, et al., Electrocardiographic, Cardiovascular and Sympatholytic Action of Dronedarone, a New Antiarrhythmic Agent, in Conscious Dogs, J Mol Cell Cardiol (1998) 30 (6) p. A3 (Abstract 2).
Bertuso, et al., Do Patients With Cardiac Arrest and Hypoalemia Require Antiarrhythmic-Drug Therapy?, American Heart Association Monograph, American Heart Association, (1984), vol. 107, pp. II-443—abstract No. 1777.
Bolderman, et al., Determination of the class III antiarrhythmic drugs dronedarone and amiodarone, and their principal metabolites in plasma and myocardium by high-performance liquid chromatography and UV-detection, Journal of Chromatography B, 877 (2009) pp. 1727-1731.
Bollmann, et al., Antiarrhythmnic Drugs in Patients with Implantable Cardioverter-Defibriliators, Am J Cardiovasc Drugs (2005) 5 (6) pp. 371-378.
Boriani, et al., Pharmacological Cardioversion of Atrial Fibrillation. Current Management and Treatment Options, Drugs (2004) 64 (24) pp. 2741-2762.
Boyd, et al., Dronedarone: Boon or bust?, Cardiology Review (2008) 25 (8) pp. 48-51.
Bril, et al., Recent advances in arrhythmia therapy: treatment and prevention of atrial fibrillation, Curr Opinion Pharmacol (2002) 2 pp. 154-159.
Butte, et al., [Amiodaron for treatment of perioperative cardiac arrythmia: a broad spectrum antiarrythmetic agent?]. Amiodaron zur Therapie perioperativer kardialer Rhythmusstorungen : Ein Breitspektrumantiarrhythmikum? , Der Anaesthesist, (Dec. 2008) vol. 57, No. 12, pp. 1183-1192.
Camm, Clinical differences between the newer antiarrhythmic agents, Europace Supplements (2000) 1 (Suppl. C) pp. C16-C22.
Camm, Safety considerations in the pharmacological management of atrial fibrillation, Int. J. Cardiol. (2008) 127 (3) pp. 299-306.
Camm, et al., New antiarrhythmic drugs for atrial fibrillation: Focus on dronedarone and vemakalant, J Interv Card Electrophysiol (2008) 23 (1) pp. 7-14.
Camm, Heart Failure and Sudden Death: Future Use of Antiarrhythmic Drugs and Devices, European Heart Journal Supplements, (2003), vol. 5, (Supplement I), pp. 1108-1115.
Castro, et al., New Antiarrhythmic Drugs for the Treatment of Atrial Fibrillaton, J Pacing and Clinical Eleotrophysiol (2002) 25 (2) pp. 249-259.
Celestino, et al., Acute in vitro effects of dronedarone, an iodine-free derivative, and amiodarone, on the rabbit sinoatrial node automaticity: a comparative study, J Cardiovasc Pharmacol and Therapeutics (2007) 12 (3) pp. 248-257.
Chatelain, et al., Interaction of the antiarrhythmic agents SR 33589 and amiodarone with the beta-adrenoceptor and adenylate cyclase in rat heart, Br J Pharmacol (1995) 116 pp. 1949-1956.
Coceani. Andromeda's Forgotten Glimmer, J Cardiovascular Electrophysiology (2006)17 (12) pp. E11.
Coleman, et al., Dronedarone: An antiarrhythmic agent for the management of atrial fibrillation and atrial flutter, Formulary (2009) 44 (2) pp. 40-46.
Coletta, et al., Clinical Trials update from Heart Rhythm 2008 and Heart Failure 2008: Athena, Urgent, INH study, Heart and CK-1827452, Eur J Heart Failure (2008) 10 pp. 917-920.
Coletta, et al., Clinical trials update from the Heart Failure Society of America and the American Heart Association meetings in 2008: SADHART-CHF, Compare, Momentum, thyroid hormone analogue study, HF-Action, I-Preserve, B-interferon study, Bach, and Athena, Eur. J Heart Failure (2009) 11(2) pp. 214-219.
Connolly, Effect of Dronedarone on Stroke and Other Cardioovascular Outcomes, (Sep. 2008) Retrieved from the Internet: URL:http://resources.escardio.org/Webcast/ESC-2008/4482, [Retrieved on Feb. 6, 2012].
Connolly, S., et al., Comparison of B-Blockers. Amiodarone Plus B-Blockers, or Sotalol for Prevention of Shocks From Implantable Cardioverter Defibrillators: The Optic Study: a Randomized Trial, JAMA, vol. 295, No. 2, pp. 165-171, (2006).
Conway, et al., New Horizons in Antiarrhythmic Therapy: Will Novel Agents Overcome Current Deficits?, Am. J. Cardiol. (2008) 102 (Suppl) 6A pp. 12H-19H.
Cooper, et al., Diuretics and risk of Arrhythmic Death in Patients With Left Ventricular Dysfunction, Circulation (1999) 100 pp. 1311-1315.
Cosnier, et al., Amiodarone and Dronedarone Reduce Early Mortality in Post MI Rat, Fundam Clin Pharmacol (1999) 13 (Suppl. 1) pp. 73S (Abstract S35.7).
Cosnier-Pucheu, et al., Effects of Serum Albumin on Amiodarone and Dronedarone Tissue Distribution and Cardiac Function in the Perfused Rat Heart, Arch. Pharmacol., (vol. 358, No. 1, Suppl. 2, (1998) p. 36.29.
Crijns, et al., Effects of Dronedarone on Clinical Outcomes in Patients with Atrial Fibrillation and Coronary Heart Disease: Insights from the ATHENA Study, Eur Heart J (2009) 30 (Suppl) p. 450 (Abstract 2779).
Dai, Two patterns of ion channelopathy in the myocardium: Perspectives for development of anti-arrhythmic agents, Curr Opin Investig Drugs (2005) 6 (3) pp. 289-297.
Dale, et al., Dronedarone: an Amiodarone Analog for the Treatment of Atrial Fibrillation and Atrial Flutter, Annals of Pharmacotherapy (2007) 41 (4) pp. 599-605.
Damy, et al., Pharmacokinetic and pharmacodynamic interactions between metoprolol and dronedarone in extensive and poor CYP2D6 metabolizers healthy subjects, Fundamental & Clinical Pharmacol (2004) 18 pp. 113-123.
Damy, et al., Pharmacokinetic and pharmacodynamic interactions between metoprolol and dronedarone in healthy subjects, Fundamental & Clin Pharmacol (2003) 17 pp. 255 (Abstract P-170).
Davy, et al., Dronedarone for the control of ventricular rate in permanent atrial fibrillation: The Efficacy and safety of Dronedarone for The control of ventricular rate during atrial fibrillation (ERATO) study, American Heart Journal (2008) 156 (3) pp. 527.e1-527.e9.

(56) References Cited

OTHER PUBLICATIONS

Davy, et al., Effect of Dronedarone on Exercise in Patients with Permanent Atrial Fibrillation, Eur. Heart J (2006) 27 (Suppl. 1) pp. 885 Abstract P5154.
Davy, et al., The efficacy and safety of dronedarone as a novel rate control agent for the treatment of atrial fibrillation, Eur Heart J (2005) 26 (Suppl. 1) pp. 505 Abstract P3042.
Davy, et al., [Atrial antiarrhythmics: Perspectives]. Antiarythiniques a l'etage atrial: Perspectives, Archives des Maladies du Coeur et des Vaisseaux, (Dec. 2006) vol. 99, No. SPEC. ISS. 5, pp. 23-29.
Dickstein, et al., Effects of losartan and captopril on mortality and morbidity in high-risk patients after acute myocardial infarction: the OPTIMAAL randomised trial, Lancet, 2002 (360) pp. 752-760.
Djandjighian, et al., Hemodynamic and Antiadrenergic Effects of Dronedarone and Amiodarone in Animals with a healed Myocardial Infarction, J Cardiovasc Pharmacol (2000) 36 (3) pp. 376-383.
Doggrell, et al., Dronedarone: an amiodarone analogue, Expert Opin Investig Drugs (2004) 13 (4) pp. 415-426.
Doyle, et al., Benefits and Risks of Long-Term Amiodarone Therapy for Persistent Atrial Fibrillation: A Meta-Analysis, Mayo Clin. Proc., vol. 84, pp. 234-242, (2009).
Echt, et al., Mortality and Morbidity in Patients Receiving Encainide, Flecainide, or Placebo, The New England Journal of Medicine, vol. 324, No. 12, (1991). pp. 781-788.
Ecker-Schlipf, et al., [Antiarrhythmics: Dronedarone—An alternative to amiodarone, but with less side effects?]. Antiarrhythmika: Dronedaron: Nebenwirkungsarmere alternative zu amiodaron?. , Krankenhauspharmazie, (Nov. 2008) vol. 29, No. 11, pp. 513-515.
Ehrlich, et al., Atrial-selective pharmacological therapy for atrial fibrillation. hype or hope?, Cur. Opin. Cardiol. (2009) 24 (1) pp. 50-55.
Ehrlich, et al., Novel Approaches for Pharmacological Management of Atrial Fibrillation, Drugs, (2009) 69 (7) pp. 757-774.
Elizari, Pure Class III and Multiclass Antiarrhythmics: Electrophysiologic Remarks and Therapeutic Experiences (A326R0110), 9th Int'l Congress on Cardiovasc Pharmacotherapy (2000) pp. 113-121.
Fessler, [Heart arrhythmia: Dronedarone as alternative to amiodarone in atrial fibrillation]. Herzrhythmusstorungen: Dronedaron: Alternative zu amiodaron bei vorhoffllmmem, Deutsche Apotheker Zeitung, (Oct. 14, 2004) vol. 144, No. 42, pp. 41-43.
Fikret, [Stabilization of sinus rhythm with dronedarone in patients with atrial fibrillation? Comment: The safety of dronedarone has not been definitively clarified]. Rhythmusstabilisierung mit dronedaron bei patienten mit vorhofflimmem? Kommentar: Sicherheit von dronedaron noch nicht abschliessend geklart., Deutsche Medizinische Wochenschrift, (Nov. 9, 2007) vol. 132, No. 45, pp. 2363.
Finance, et al., Effects of a New Amiodarone-Like Agent, SR 35589, in Comparison to Amiodarone, D,L-Sotaiol, and Lignocaine, on Ischemia-Induced Ventricular Arrhythmias in Anesthetized Pigs, J Cardiovasc Pharmacol (1995) 26 (4) pp. 570-576.
Finance, et al., Eiectrophysiological and Anti-Arrhythmic Actions of a New-Amiodarone-Like Agent, Dronedarone in Experimental Atrial Fibrillation, J Mol Cell Cardiol (1998) 30 (7) p. A251 (Abstract 74).
Finance, et al., Electrophysiological and Hemodynamic Effects of a New Amiodarone-Like Agent Following Acute and Chronic Oral Treatment in Anesthetized Dogs, J Mol Cell Cardiol (1998) 30 (7) p. A251 (Abstract 75).
Franzosi, et al., Indications for ACE Inhibitors in the Early Treatment of Acute Myocardial Infarction: Systematic Overview of Individual Data From 100 000 Patients in Randomized Trials, Circulation, 1998 (97) pp. 2202-2212.
Gage, et al., Selecting Patients With Atrial Fibrillation for Anticoagulation: Stroke Risk Stratification in Patients Taking Aspirin, Circulation. (2004), vol. 110, pp. 2287-2292.
Gautier, et al., Electrophysiologic Characterization of Dronedarone in Guinea Pig Ventricular Cells, J Cardiovasc Pharmacol (2003) 41 pp. 191-202.
Gautier, et al., In Vivo and In Vitro Characterization of the Novel Antiarrhythmic Agent SSR149744C. Electrophysiological, Anti-Adrenergic, and Anti-Angiotensin II Effects, J Cardiovasc Pharmacol (2004) 44 (2) pp. 244-257.
Gautier, et al., In Vivo and In Vitro Antiarrhythmic Effects of SSR149744C in Animal Models of Atrial Fibrillation and Ventricular Arrhythmias, J Cardiovasc Pharmacol (2005) 45 (2) pp. 125-135.
Gautier, et al., Electrophysiological Characterization of Dronedarone (SR 33589), A New Amiodarone-Like Agent, In Cardiac Ventricular Myocytes, Eur. Heart J., (18. Abstr Suppl., 269, 1997) (Abstract P1589).
Gensthaler, et al., [Dronedarone—A new hope for patients with atrial fibrillation]. Dronedaron—Neue hoffnung bei Vorhofflimmern, Pharmazeutische Zeitung, (Sep. 11, 2008) vol. 153, No. 37, p. 34.
Groch, New Antiarrhythmic Agent Shows Promise for A-Fib, http://www.medpagetoday.com/Cardiology/Arrhythmias/6598, pp. 1-3, (2007).
Groenefeld, et al., Dronedarone as relapse prophylaxis after cardioversion of atrial fibrillation: results of a randomised, placebo-controlled, dose-finding study, Z.Kardiol. (92, Suppl. 1, V601, 2003).
Guillemare, et al., Acute Effects of Dronedarone and Amiodarone on iK1, iKr and iKs in Guinea Pig Ventricular Myocytes, Fundam. Clin. Pharmacol. (1999) 13 p. 388 (Abstracts—French Pharmacological Society).
Guillemare, et al., Inhibitory Effects of Dronedarone on Muscarinic K+ Current in Guinea Pig Atrial Cells, J Cardiovasc Pharmacol (2000) 36 (6) pp. 802-805.
Guillemare, et al., Effects of Dronedarone on Calcium Handling in Cardiac Ventricular Myocytes, Eur. Heart J. Supplements vol. 1, (20, Abstract Suppl., 329, 1999) (Abstract P1749).
Guiraudou, et al., Involvement of Nitric Oxide in the Coronary Vasodilation Induced by Amiodarone and Dronedarone in the Isolated Guinea Pig Heart, Fundam Clin Pharmacol (1999) 13 (Suppl. 1) pp. 73S (Abstract S35.8).
Guiraudou, et al., Involvement of nitric oxide in amiodarone- and dronedarone-induced coronary vasodilation in guinea pig heart, Eur J Pharmacol (2004) 496 pp. 119-127.
Guiraudou, et al., Nitric oxide-dependent coronary relaxant effect of amiodarone and dronedarone in the isolated guinea pig heart, Archives of Pharmacol (1998) 358 pp. R299 (Abstract P18. 16).
Gupta, et al., Newer Antiarrhythmic Drugs, Indian Heart J (2001) 53 pp. 354-360.
Han, et al., Benzofuran derivatives and the thyroid, Clinical Endocrinology (2009) 70 pp. 2-13.
Hodeige, et al., SR 33589, a new amiodarone-like antiarrhythmic agent: anti-adrenoceptor activity in anaesthetized and conscious dogs, Eur J Pharmacol (1995) 279 pp. 25-32.
Hodeige, et al., SR 33589—Effect on Atrial Fibrillation in Dogs: Comparison With Amiodarone, European Section Meeting, International Societ for Heart Research, 15th, Copenhagen, Jun. 8-11, 1994, Meeting Date 1994, 681-684.
Hohnloser, et al., Correction—Effect of dronedarone on cardiovascular events in atrial fibrillation, NEJM (2009) 360 (23) pp. 2487.
Hohnloser, et al., Dronedarone Significantly Decreases the Combined Endpoint of Hospitalization and Death in Patients with Atrial Fibrillation, Circulation (2005) 112(17) Supp II pp. II-327-II 328 (Abstract 1637).
Hohnloser, et al., Effect of Dronedarone on Cardiovascular Events in Atrial Fibrillation, NEJM (2009) 360 (7) pp. 668-678.
Hohnloser, et al., Effect of Dronedarone on Cardiovascular Outcomes: A Meta-analysis of Five Randomized Controlled Trials in 6157 Patients With Atrial Fibrillation/Flutter, J Am. Coll. Cardiol. (2009) 53 (10) Suppl. 1; e-Abstract 1020-54 pp. 1-7.
Hohnloser, et al., Rationale and Design of ATHENA: A Placebo-Controlled Double-Blind, Parallel Arm Trial to Assess the Efficacy of Dronedarone 400 mg Bid for the Prevention of Cardiovascular Hospitalization or Death from any Cause in Patients with Atrial Fibrillation/Atrial Flutter, J Cardiovasc Etectrophysiol (2008) 19 pp. 69-73.
Huang, Pharmacological cardioversion of atrial fibrillation, Zhongguo Xinyao Yu Linchuang Zazhi (2007), 26(8), 631-635.
Hynes, et al., A review of the pharmacokinetics, electrophysiology and clinical efficacy of dronedarone, Future Cardiology (2005) 1 (2) pp. 135-144.
Indik, et al., The Patient with Atrial Fibrillation, American J Med. (2009) 122 (5) pp. 415-418.

(56) References Cited

OTHER PUBLICATIONS

Iqbal, et al., Recent developments in atrial fibrillation, Br Med J (2005) 330 pp. 238-243.
Ishii, et al., Effects of dronedarone on the currents of Xenopus oocytes co-expressing HERG and KvLQt1/mink channels, J Mol Cell Cardiol (2005) 39 (6) pp. 1017-1018 (Abstract P-2-4).
Iwamoto, et al., Na+/Ca2+ exchange inhibitors: a new class of calcium regulators, Cardiovas. & Hematolog. Disorders: Drug Targets (2007) 7 (3) pp. 188-198.
Kathofer, et al., The Novel Antiarrhythmnic Drug Dronedarone: Comparison with Amiodarone, Cardiovascular Drug Reviews (2005) 23 (3) pp. 217-230.
Kayser, Dronedarone: In Quest of the Ideal Antiarrhythmic Drug, Prog. in Cardiovasc. Nursing (2007) 22 (4) pp. 221-224.
Khan, Oral class III antiarrhythmics: what is new?, Current Opin Cardiology (2004) 19 pp. 47-51.
Khoo, et al., Acute Management of Atrial Fibrillation, Chest (2009) 135 (3) pp. 849-859.
Klein, et al., [Dronedarone—A new therapeutic option for controlling atrial rhythm and ventricular frequency]. Dronedaron—Eine neue therapeutische option zur kontrolle von vorhofrhythmus und kammerfrequenz. , Deutsche Medizinische Wochenschrift, (Sep. 8, 2006) vol. 131, No. 34-35 Suppl., pp. S113-S117.
Koeber, et al., Increased Mortality after Dronedarone Therapy for Severe Heart Failure, NEJM (2008) 358 (25) pp. 2678-2687.
Kopceuch, ATHENA trial post hoc analysis shows dronedarone significantly reduced hospitalization incidence and duration, Cardiology Review, 26 (1) 2009 pp. 39.
Krishnamoorthy, et al., Antiarrhythmic drugs for atrial fibrillation: focus on dronedarone, Expert Rev. Cardiovasc. Therapy (2009) 7 (5) pp. 473-481.
Lafuente, et al., Antiarrhythmic Drugs for Maintaining Sinus Rhythm After Cardioversion of Atrial Fibrillation—A Systematic Review of Randomized Controlled Trials, Arch Intern Med (2006) 166 pp. 719-728.
Lagorce, et al., Simultaneous Electrospray LC/MS/MS Assay Method of Dronedarone (SR33589) and its Debutyl Metabolite (SR35021) in Human Plasma, J Pharm Belg (1998) 53 (10) pp. 210 (Abstract).
Lalevee, et al., Effects of Amiodarone and Dronedarone on Voltage-Dependent Sodium Current in Human Cardiomyocytes, J Cardiovasc Electrophysiol (2003) 14 pp. 885-890.
Laughlin, et al., Dronedarone: A New Treatment for Atrial Fibrillation, J. Cardiovasc. Electrophysiol. (2008) 19 (11) pp. 1220-1226.
Le Grand, Dronedarone, Sanofi-Synthelabo, Current Opinion in Cardiovascular, Pulmonary & Renal Investigational Drugs, (2000), vol. 2, No. 1, pp. 36-39.
Le Grand, Dronedarone, IDrugs (2001) 4 (5) pp. 582-585.
Lee et al., IKr Channel Stockers: Novel Antiarrhythmic Agents, Curr Med Chem—Cardiovascular & Hematological Agents (2003) 1 pp. 203-223.
Lewalter, et al., Pharmacotherapy of supraventriculair arrhythmias, Internist (47, No. 1, 80-1,83-8, (2006).
Liu, et al., Dronedarone: A novel antiarrhythmic drug for the treatment of atrial fibrillation. , Pharmaceutical Care and Research, (Dec. 2008) vol. 8, No. 6, pp. 417-420.
Lombardi, et al., Pharmacological Treatment of Atrial Fibrillation: Mechanisms of Action and Efficacy of Class III Drugs, Current Med Chem (2006) 13 (14) pp. 1635-1653.
Manning, et al., SR 33589, a New Amiodarone-Like Agent: Effect on Ischemia- and Reperfusion-Induced Arrhythmias in Anesthetized Rats, J Cardiovas Pharmacol (1995) 26 (3) pp. 453-461.
Manning, et al., SR 33589, a New Amiodarone like Antiarrhythmic Agent: Eiectrophysiological Effects in Anesthetized Dogs, J Cardiovasc Pharmacol (1995) 25 (2) pp. 252-261.
Manoach, et al., Hypokalema as a Simple Reproducible Model for Sustained Atrial Fibrillation, J Mol and Cell Cardiology (1998) 30(6) p. A4 (Abstract 8).
Mealy, et al., Dronedarone Hydrochloride, Drugs Fut (2005) 30 (4) pp. 397-398.

Moro, et al., In Vitro Effects of Acute Amiodarone and Dronedarone on Epicardial, Endocardial, and M Cells of the Canine Ventricle, J Cardiovasc Pharmacol. Therapeutics (2007) 12 (4) pp. 314-321.
Morrow, et al., Drug Therapy for Atrial Fibrillation: What Will Its Role Be in the Era of Increasing Use of Catheter Ablation?, PACE, 32(1) 2009 pp. 108-118.
Morrow, et al., New antiarrhythmic drugs for establishing sinus rhythm in atrial fibrillation. What are our therapies likely to be by 2010 and beyond?, Am Heart J (2007) 154 (5) pp. 824-829.
Muller, et al., Clinical trial updates and hotline sessions presented at the European Society of Cardiology Congress 2008, Clin. Res. Cardiol. (2008) 97 (12) pp. 851-864.
Naccarelli, et al., Atrial fibrillation and the expanding role of catheter ablation: Do antiarrhythmic drugs have a future?, J. Cardiovasc. Pharmacol. (2008) 52 (3) pp. 203-209.
Naccarelli, et al., New antiarrhythmic treatment of atrial fibrillation, Expert Rev. of Cardiovasc. Ther. (2007) 5 (4) pp. 707-714.
Naccarelli, et al., Old and New Antiarrhythmic Drugs for Converting and Maintaining Sinus Rhythm in Atrial Fibrillation: Comparative Efficacy and Results of Trials, Am J Cardiol (2003) 91 (suppl) pp. 15D-26D.
Nattel, et al., New Approaches to Atrial Fibrillation Management. A Critical Review of a Rapidly Evolving Field, Drugs (2002) 62 (16) pp. 2377-2397.
Norota, et al., Inhibitory effects of dronedarone and amiodarone on HERG+KvLQT1/minK currents, J Pharmacol Sci (2006) 100 (Suppl. 1) pp. 221P Abstract P2M-08.
Ocasio, et al., Clinical prospects for new thyroid hormone analogues, Curr Opinion Endocrinol and Diabetes (2005) 12 pp. 363-370.
Pantos, et al., Blockage of thyroid hormone receptor alpha 1 suppresses food intake and potentiates thyroxine effect on body weight reduction, Eur Heart J (2005) 26 (Suppl. 1) p. 608, Abstract P3612.
Pantos, et al., Dronedarone Administration Prevents Body Weight Gain and Increases Tolerance of the Heart to Ischemnic Stress: A Possible Involvement of Thyroid Hormone Receptor alpha1, Thyroid (2005) 15 (1) pp. 16-23.
Pantos, et al., Effects of dronedarone and amiodarone on plasma thyroid hormones and on the basal and postischemic performance of the isolated rat heart, Eur J Pharmacol (2002) 444 pp. 191-196.
Pantos, et al., Pharmacological inhibition of TRalpha1 receptor potentiates the thyroxine effect on body weight reduction in rats: potential therapeutic implications in controlling body weight, Diabetes, Obesity & Metabolism (2007) 9 (1) pp. 136-138.
Pantos, et al., Thyroid Hormone Receptor A1: A New Pharmacological Target for Cardioprotection and Body Weight Control, Epitheorese Klin. Farmakol. Farmakokinet. (2008) 26 (1) pp. 36-37.
Pecini, et al., New antiarrhythmic agents for atrial fibrillation and atrial flutter, Expert Opin Emerging Drugs (2005) 10 (2) pp. 311-322.
Pedersen, et al., The immediate future for the medical treatment of atrial fibrillation, Expert Opin Emerging Drugs (2002) 7 (2) pp. 259-268.
Pfeffer, et al., Effect of Captopril on Mortality and Morbidity in Patients with Left Ventricular Dysfunction After Myocardial Infarction, NEJM, 1992 (327) 10 pp. 669-677.
Phillips, et al., Clinical Disorders of Potassium Homeostasis: Hyperkalemia and Hypokalemia, Veterinary Clinics of North America: Small Animal Practice, vol. 28, No. 3, pp. 545-564, (1998).
Pitt, et al., Chronic amiodarone-induced inhibition of the Na+-K+ pump in rabbit cardiac myocytes is thyroid-dependent: comparison with dronedarone, Cardiovascular Res (2003) 57 pp. 101-108.
Pitt, et al., Eplerenone, a Selective Aldosterone Blocker, in Patients with Left Ventricular Dysfunction after Myocardial Infarction, NEJM, 2003 (348) 14 pp. 1309-1321.
Pitt, et al., The Effect of Spironolactone on Morbidity and Mortality in Patients with Severe Heart Failure, NEJM, 1999 (341) 10 pp. 709-717.
Pollak, et al., Creatinine elevation in patients receiving amiodarone correlates with serum amiodarone concentration, Br J Clin Pharmac, 1993 (36) pp. 125-127.
Pollak, et al., Changes in Serum Urea and Creatinine During Long-Term Therapy with Amiodarone, Clinical Pharmacology and Therapeutics, vol. 75, No. 2, p. 5, p. I-9, (2004).

(56) References Cited

OTHER PUBLICATIONS

Preobrazhenskii, How Did Athena Win Andromeda? Results of the Athena, Kardiologila, (2009), vol. 49, No. 4, pp. 63-64.
Preobrazhenskii, et al., Efficacy of dronedarone in cardiac failure due to severe left ventricular systolic dysfunction. Results of the Andromeda, Kardiologiia, (2008) vol. 48, No. 12, p. 67.
Preobrazhenskii, et al., Efficacy of dronedarone for maintenance of sinus rhythm in atrial fibrillation or flutter, Results of the EURIDIS and ADONIS, Kardiologiia, (2008) vol. 48, No. 7, pp. 58-59.
Prystowsky, et al., Case Studies with the Experts: Management Decisions in Atrial Fibrillation, J. Cardiovasc Electrophysiol, vol. 19, pp. 1-12, Suppl. 1, (2008).
Purerfellner, et al., Athena-Studie: Vorlaufige Ergebnisse und Deren Mogliche Auswirkungen auf die Antiarrhythmische Pharmakotherapie bei Vorhofflimmern, Journal Fuer Kardiologie, Krause Und Pachernegg. vol. 15, No. 7-8, (2008), pp. 253-254.
Quaglino, et al., Effects of metabolites and analogs of amiodarone on alveolar macrophages: structure-activity relationship, Am J Physiol Lung Cell Mol Physiol (2004) 287 pp. L438-L447.
Ridley, et al., High affinity HERG K+ channel blockade by the antiarrhythmic agent dronedarone: resistance to mutations of the S6 residues Y652 and F656, Biochem Biophys Research Comm (2004) 325 pp. 883-891.
Riera, et al., Relationship among amiodarone, new class III antiarrhythmics, miscellaneous agents and acquired long QT syndrome, Cardiology Journal (2008) 15 (3) pp. 209-219.
Rocchetti, et al., Cellular Electrophysiological Study of Dronedarone, a New Amiodarone-Like Agent, in Guinea Pig Sinoatrial Node, Archives of Pharmacology (1998) 358 (Suppl.2) pp. R617 (Abstract P 36.13).
Rochetaing, et al., Beneficial Effects of Amiodarone and Dronedarone (SR 33589b), when Applied During Low-Flow Ischemia, on Arrhythmia and Functional Parameters Assessed during Reperfusion in isolated Rat Hearts, J Cardiovasc Pharmacol (2001) 38 (4) pp. 500-511.
Roy, et al., Rythm Control Versus Rate Control for Atrial Fibrillation and Heart Failure, The New England Journal of Medicine, vol. 358, No. 25, pp. 2667-2677, (2008).
Sablayrolles, et al., Drug evaluation: Dronedarone, a novel non-iodinated anti-arrhythmmic agent, Current Opinion in investigational Drugs (2006) 7 (9) pp. 842-849.
Sarma, et al., Dose-Dependent Effects of Dronedarone on the Circadian Patterns of RR and QT Intervals in Healthy Subjects, Circulation, (102, No. 18, Suppl. 802, 2000).
Schauerte, et al., Drug therapy of atrial fibrillation, Med.Welt (56, No. 9, 375-375, 2005).
Schmitt, et al., New Antiarrhythmic Drugs for the Treatment of Atrial Fibrillation, Herz (2008) 33 (8) pp. 562-567.
Schwender, [Dronedarone establishes and maintains control of sinus rhythm]. Controle du rythme en cas de fibrillation auriculaire. La dronedarone retablit et maintient le rythme sinusal, Revue medicale suisse, (Aug. 23, 2006) vol. 2, No. 76, pp. 1902-1903.
Seelig, et al., Nephrotoxicity Associated with Concomittant ACE Inhibitor and NSAID Therapy, Southern Medical Journal, vol. 83, No. 10, pp. 1144-1148, (1990).
Serre, et al., Lack of proarrhythmic effect of dronedarone and amiodarone in a rabbit model of torsades de pointes, Comparison with dofetilide, Fundamental & Clinical Pharmacol (2001) 15 (Suppl. 1) p. 45 (Abstract 7P202).
Shi, et al., Long-term Effects of Amiodarone and its Non iodinated Analogue, Dronedarone, on the Transcription of Cardiac Sarcoplasmic Reticulum Ca2+—ATPase Gene, Environmental Med (2003) 47 pp. 39-41.
Shimizu, et al., Effects of Dronedarone on HERG and KCNQ1/KCNE1 Channels, Environmental Med (2003) 47 pp. 48-50.
Sicouri, et al., Dronedarone and Amiodarone Reduce Transmural Dispersion of Repolarization in the Canine Heart, Fundam Clin Pharmacol (1999) 13 (Suppl. 1) p. 72S (Abstract S35.5).
Singh, Trials of New Antiarrhythmic Drugs for Maintenance of Sinus Rhythmn in Patients with Atrial Fibrillation, J Intervent Cardiac Electrophysiol (2004) 10 pp. 71-76.
Singh, Amiodarone as Paradigm for Developing New Drugs for Atrial Fibrillation, J Cardiovasc Pharmacol (2008) 52 (4) pp. 300-305.
Singh, Amiodarone: A Multifaceted Antiarrhythmic Drug, Current Cardiology Reports (2006) 8 pp. 349-355.
Singh, et al., Dronedarone for Maintenance of Sinus Rhythm in Atrial Fibrillation or Flutter, NEJM (2007) 357 (10) pp. 987-999.
Singh, et al., Dronedarone: rhythm and rate control in management of atrial fibrillation. Focus on Symptomatic Arrhythmia, Eur. Heart J (2006) 27 (Suppl. 1) p. 33 Abstract P440.
Singh, et al., Mechanisms of Action of Antiarrhythmic Drugs Relative to the Origin and Perpetuation of Cardiac Arrhythmias, J Cardiovasc Pharmacol Therapeut (2001) 6 (1) pp. 69-87.
Singh, et al., Mechanisms of Antiarrhythmic Actions in the Maintenance of Sinus Rhythm in Patients with Atrial Fibrillation: Clinical and Experimental Correlations, Atrial Fibrillation: New Therapeutic Concepts, Papp et al., Eds., (2003) pp. 41-55.
Stein, Dronedarone Provides Multiple Benefits in Atrial Fibrillation: Presented at AHA, Doctor's Guide Personal Edition, 2 pages. (2005).
Stiles, et al., FDA Advisory Panel Recommends Dronedarone Approval for Atrial Fibrillation, (2009). URL: www.theheart.org/article/949121.do [retrieved on Jul. 21, 2010].
Stoykov, et al., Effect of amiodarone and dronedarone administration in rats on thyroid hormone-dependent gene expression in different cardiac components, Eur J of Endocrinology (2007) 156 (6) pp. 695-702.
Sun, et al., Acute Effects of Dronedarone on Potassium Currents in Isolated Rabbit Ventricular Myocytes. Comparison With Amiodarone, J Am Coll Cardiol (2000) 2 (Suppl. A) p. 98A (Abstract 1030-99).
Sun, et al., Acute Effects of Dronedarone on the Potassium Currents in Human Atrial Cells, J Am Coll Cardiol (2002) 39 (5) Suppl. A, p. 105A (Abstract 1136-115).
Sun, et al., Chronic and Acute Effects of Dronedarone on the Action Potential of Rabbit Atrial Muscle Preparations: Comparison With Amiodarone, J Cardiovascul Pharmacol (2002) 39 (5) pp. 677-684.
Sun, et al., Dronedarone Acutely Inhibits L-Type Calcium Currents and Alters the Channel Kinetics in Rabbit Ventricular Myocytes, J Am Coll Cardiol (2001) 37 (Suppl. A) p. 114A (Abstract 1202-112).
Sun, et al., Electrophysiological Effects of Dronedarone (SR33589), a Noniodinated Benzofuran Derivative, in the Rabbit Heart: Comparison With Amiodarone, Circulation (1999) 100 pp. 2276-2281.
Swedberg, et al., Effects of the Early Administration of Enalapril on Mortality in Patients with Acute Myocardial Infarction, NEJM, 1992 (327) 10 pp. 678-684.
Tafreshi, et al., A Review of the Investigational Antiarrhythmic Agent Dronedarone, J of Cardiovasc. Pharmacol. and Therapeutics (2007) 12 (1) pp. 15-26.
Tamargo, et al., Pharmacology of cardiac potassium channels, Cardiovascular Res. (2004) 62 pp. 9-33.
Tedelind, et al., Amiodarone Inhibits Thyroidal Iodide Transport In Vitro by a Cyclic Adenosine 5'-Monophosphate- and Iodine-Independent Mechanism, Endocrinology (2006) 147 (6) pp. 2936-2943.
Tejani, et al., [Correspondence Related to Hohnloser et al, NEJM (2009) 360 pp. 668-678] Dronedarone on Atrial Fibrillation, NEJM (2009) 360 (23) pp. 2479-2481.
Thomas, et al., Acute effects of dronedarone on both components of the cardiac delayed rectifier, K+ current, HERG and KvLQT1/minK potassium channels, Br J Pharmacol (2003) 140 pp. 996-1002.
Touboul, et al., Dronedarone for prevention of atrial fibrillation: A dose-ranging study, Eur Heart J (2003) 24 pp. 1431-1487.
Touboul, et al., [New anti-arrythmics—Hope or disappointment?]. Nouveaux anti-arythmiques—Espoir ou deception?, Archives des Maladies du Coeur et des Vaisseaux, (Nov. 2004) vol. 97, No. 11, pp. 1048-1053.
Tschuppert, et al., Effect of Dronedarone on Renal Function in Healthy Subjects, Br. J. Clinical Pharmacol. (2007) 64 (6) pp. 785-791.

(56) References Cited

OTHER PUBLICATIONS

Van Beeren, et al., Dronedrarone Acts as a Selective Inhibitor of 3,5,3'-Triiodothyronine Binding to Thyroid Hormone Receptor-alpha1: In Vitro and in Vivo Evidence, Endocrinology (2003) 144 (2) pp. 552-558.
Van Opstal, et al., Chronic Amiodarone Evokes No Torsade de Pointes Arrhythmias Despite QT Lengthening in an Animal Model of Acquired Long-QT Syndrome, Circulation (2001) 104 pp. 2722-2727.
Vanoli, et al., Dronedarone, A New Amiodarone-Like Compound, Prevents Ventricular Fibrillation in Conscious Dogs with a Healed Myocardial Infarction, Fundam Clin Pharmacol (1999) 13 (Suppl. 1) pp. 73S (Abstract S35.6).
Vanoli, et al., Dronedarone, A New Amiodarone-Like Compound, Prevents Ventricular Fibrillation in Conscious Dogs With a Healed Myocardial Infarction, Circulation, (98, No. 17, Suppl.1817, 1998) (Abstract 4286).
Varro, et al., Comparison of the Cellular Electrophysiological Effects of Amiodarone and Dronedarone in Canine Ventricular Muscle and Purkinje Fibers, Fundam Clin Pharmacol (1999) 13 (Suppl. 1) pp. 72S (Abstract S35.4).
Varro, et al., Electrophysiological effects of dronedarone (SR33589), a noniodinated amiodarone derivative in the canine heart: comparison with amiodarone, Br J Pharmacol (2001) 133 pp. 625-634.
Varro, et al., Pharmacology of Potassium Channel Blockers, Atrial Fibrillation: New Therapeutic Concepts, Papp et al., Eds., (2003) pp. 27-39.
Varro, et al., The cellular cardiac electrophysiologial effects of dronedarone a new amiodarone like antiarrhythmic agent, Cardiovasc Drugs and Therapy (2000) 14 (2) p. 206 (Abstract 200).
Varro, et al., Theocretical Possibilities for the Development of Novel Antiarrhythmic Drugs, Current Med Chem (2004) 11 pp. 1-11.
Verduyn, et al., Evaluation of the Acute Electrophysiologic Effects of Intravenous Dronedarone, an Amiodarone-Like Agent, with Special Emphasis on Ventricular Repolarization and Acquired Torsade de Pointes Arrhythmias, J Cardiovasc Pharmacol (1999) 33 (2) pp. 212-222.
Vos, Preclinical Evaluation of Antiarrhythmic Drugs: New Drugs Should be Safe to be Successful, J Cardiovasc Electrophysiol (2001) 12 (9) pp. 1034-1036.
Vos, et al., Anti-Arrhythmic Drugs and Torsade de Pointes Arrhythmias: An Experimental Approach, Fundam Clin Pharmacol (1999) 13 (Suppl. 1) pp. 71S (Abstract S35.2).
Vos, et al., Absence of Torsade de Pointes Arrhythmias Despite QT-Lengthening After Oral Amiodarone Treatment in an Animal Model of Acquired Long QT, Eur. Heart J., (22, Abstract Suppl. 449, 2001) (Abstract 2366).
Wadhani, et al., Dose-Dependent Effects of Oral Dronedarone on the Circadian Variation of RR and QT Intervals in Health Subjects: Implications for Antiarrhythmic Actions, J Cardiovasc Pharmacol and Therapeutics (2006) 11 (3) pp. 184-190.
Walker, Antiarrhythmic drug research, Br J of Pharmacology (2006) 147 (Suppl. 1) pp. S222-S231.
Watanabe, et al., Acute inhibitory effect of dronedarone, a noniodinated benzofuran analogue of amiodarone, on Na+/Ca2+ exchange current in guinea pig cardiac ventricular myocytes, Naunyn-Schmiedeberg's Arch. Pharmacol (2008) 377 pp. 371-376.
Watanabe, et al., Effect of dronedarone on NA+/Ca2+ exchange current: comparison with amiodarone, J Pharmacol Sci (2003) 91 (Suppl. 1) pp. 141P (Abstract 1P214).
Watanabe, et al., Inhibitory effect of dronedarone on Na+/Ca2+ exchange current in guinea pig cardiac myocytes. comparison ,with amiodarone, J Mol Cell Cardiology (2003) 35 p. A31 (Abstract P-25; 20th Annual Meeting, Inter'l Soc for Heart Research).
Watanabe, et al., Topics on the NA+/Ca2+ Exchanger: Pharmacological Characterization of Na+/Ca2+ Exchanger Inhibitors, J Pharmacol Sci (2006) 102 pp. 7-16.
Wegener, et al., Dronedarone: An Emerging Agent with Rhythm- and Rate-controlling Effects, J Cardiovasc. Electrophysiol. (2006) 17 (Supp 2) pp. S17-S20.

White, Is dronedarone effective for the prevention of recurrent atrial fibrillation?, Nature Clin Prac Cardiovasc Med (2008) 5 (3) pp. 136-137.
Wijffels, et al., Atrial Flbrillation Begets Atrial Fibrillation—A Study in Awake Chronically Instrumented Goats, Circulation (1995) 92 pp. 1954-1968.
Wood, Euridis and Adonis: Dronedarone Bests Placebo for Sinus Rhyth, but Amiodarone Comparison Data Needed, http://www.theheart.org/article/809207.doc, pp. 1-2, (2007).
Wu, et al., Medication of heart failure and atrial fibrillation, Zhongguo Shiyong Neike Zazhi (2008), 28(6), 429-431.
Wyse, Pharmacologic approaches to rhythm versus rate control in atrial fibrillation—where are we now?, Int. J Cardiology (2006) 110 pp. 301-312.
Wyse, et al., A Comparison of Rate Control and Rhythm Control in Patients with Atrial Fibrillation, The New England Journal of Medicine, vol. 347, No. 23, (2002). pp. 1825-1833.
Wyse, et al., Alternative Endpoints for Mortality in Studies of Patients with Atrial Fibrillation: The AFFIRM Study Experience, Heart Rhythm, vol. 1, pp. 531-537, (2004).
Yusuf, et al., Effects of an Angiotensin-Converting—Enzyme Inhibitor, Ramipril, on Cardiovascular Events in High-Risk Patients, NEJM, 2000 (342) 3 pp. 145-153.
Zareba, Dronedarone: A New Antiarrhythmic Agent, Drugs of Today (2006) 42 (2) pp. 75-86.
Zimetbaum, Dronedarone for Atrial Fibrillation—An Odyssey, NEJM (2009) 360 (18) pp. 1811-1813.
Zunkler, Human ether-a-go-go-related (HERG) gene and ATP-sensitive potassium channels as targets for adverse drug effects. Pharmacology & Therapeutics (2006) 112 (1) pp. 12-37.
ClinicalTrials.gov/archive—View of NCT00174785 on Sep. 14, 2005—ATHENA: A Trial with Dronedarone to Prevent Hospitalization or Death in Patients with Atrial Fibrillation, [on-line] This page was last modified on Jun. 9, 2010.
Dronedarone, Merck Index, 14th. Merck & Co. (2007),—No. 0003449, Characterizing Dronedarone as an Anti-arrhythmic, pp. 1-2.
El Tratemiento con Dronedarona en Pacientes con Arritmia Cardiaca Reduce el Numbero de Hospitalizaciones Segun un Estudio, (2005), 2 pages and English Translation thereof.
[Dronedarone for antiarrhythmic therapy]. Dronedaron zur anti-arrhythmischen therapie, Deutsche Apotheker Zeitung, (May 5, 2008) vol. 148, No. 23, pp. 47-48.
Multaq (Dronedarone) Briefing Document, Advisory Committee Meeting of the Cardiovascular and Renal Drugs Division of the US Food and Drug Administration, Mar. 18, 2009.
Preliminary Search Report, FR 0803208.
Risk Evaluation and Mitigation Strategy (REMS), (2009), http://www.fda.gov/downloads/Drugs/Drugsafety/PostmarketDrugSafetyInformationforPatientsandProvides/UCM187494.pdf.
Sanofi-Aventis: Prescribing Information, (2009), http://products.sanofi-aventis.us/Multaq/Multaq.pdf.
Summary Minutes of the Cardiovascular and Renal Drugs Advisory Committee Mar. 19, 2009, Retrieved from the Internet: URL:http://www.fda.gov/downloads/AdvisoryCommittees/committeesMeetingMaterials/Drugs/CardiovascularandRenalDrugsAdvisoryCommittee/UCM151691.pfd [retrieved on Jul. 21, 2010].
Benjamin, et al., Independent Risk Factor for Atrial Fibrillation in a Population-Based Conhort, JAMA, (1994), vol. 271, No. 11, pp. 840-844.
Khan, et al., Pharmacological Cardioversion of Recent Onset Atrial Fibrillation, European Heart Journal, (2004), vol. 25, pp. 1274-1276.
Morady, et al., The Treatment of Atrial Fibrillation, University of Michigan Electrophysiology Service, (2009), pp. 1-12.
U.S. Appl. No. 12/431,830—Final Office Action dated Jun. 7, 2011.
U.S. Appl. No. 12/431,830—Non-Final Office Action dated Oct. 29, 2010.
U.S. Appl. No. 12/951,471—Non-Final Office Action dated Jun. 22, 2012.
U.S. Appl. No. 12/962,102—Non-Final Office Action dated Jun. 18, 2012.

(56) References Cited

OTHER PUBLICATIONS

U.S. Appl. No. 12/962,115—Non-Final Office Action dated Jun. 21, 2012.
U.S. Appl. No. 12/431,830—Non-Final Office Action dated Jun. 20, 2012.
U.S. Appl. No. 13/211,673—Non-Final Office Action, dated Jun. 13, 2012.
U.S. Appl. No. 12/425,125—Non-Final Office Action dated Mar. 16, 2012.
U.S. Appl. No. 12/425,125—Final Office Action dated Aug. 8, 2011.
U.S. Appl. No. 12/425,125—Non-Final Office Action dated Nov. 24, 2010.

METHODS FOR REDUCING THE RISK OF AN ADVERSE DRONEDARONE/BETA-BLOCKERS INTERACTION IN A PATIENT SUFFERING FROM ATRIAL FIBRILLATION

The present invention relates to the use of dronedarone or pharmaceutically acceptable salts thereof, for the preparation of a medicament for use in the prevention of atrial fibrillation, and reducing the risk of an adverse drug interaction with beta-blockers such as metoprolol and propranolol.

The instant invention relates to a method of providing dronedarone or pharmaceutically acceptable salts thereof.

The instant invention also relates to a method of managing the risk of beta-blockers/dronedarone interaction.

The instant invention also relates to a method of promoting the use of dronedarone or pharmaceutically acceptable salts or esters thereof.

The instant invention also relates to an article of manufacture and a package comprising dronedarone or pharmaceutically acceptable salts or esters thereof.

2-n-Butyl-3-[4-(3-di-n-butylaminopropoxy)benzoyl]-5-methylsulphonamidobenzofuran, or dronedarone, and pharmaceutically acceptable salts thereof are described in European Patent EP 0 471 609 B1.

Dronedarone blocks potassium, sodium and calcium channels and also has anti-adrenergic properties. Dronedarone is an antiarrhythmic that is effective in maintaining sinus rhythm in patients presenting atrial fibrillation or atrial flutter.

The applicant has clinically proven that dronedarone significantly reduces cardiovascular hospitalizations and/or mortality in patients having a history of atrial fibrillation (AF) or of atrial flutter (AFL) in a safe and effective way. Dronedarone is indicated to reduce the risk of cardiovascular hospitalization in patients with paroxysmal or persistent AF or AFL, with a recent episode of AF/AFL and associated cardiovascular risk factors (i.e., age >70, hypertension, diabetes, prior cerebrovascular accident, left atrial diameter ≥50 mm or left ventricular ejection fraction [LVEF] <40%), who are in sinus rhythm or who will be cardioverted.

Beta-blockers, commonly prescribed drugs in cardiac patients, are mainly metabolized by CYP2D6. Interactions due to inhibition of beta-blockers metabolism by CYP2D6 inhibitors have been reported. Dronedarone has the potential to inhibit CYP2D6.

Beta-blockers are frequently co-prescribed as they are used for the treatment of hypertension, cardiac arrhythmias, coronary ischemia in particular post-myocardial infarction and heart failure. The coadministration of dronedarone and beta-blockers may result in an interaction that may lead to side effects such as bradycardia, heart failure and fatigue if not carefully managed. Based on the likelihood of the co-prescription of these 2 drugs and the likelihood of clinically significant interactions, an interaction study was performed.

During an interaction study with dronedarone, it has been observed that administration of this active principle together with beta-blockers is associated with an increase of steady state beta-blockers exposures, which can lead to side effects such as bradycardia, heart failure and fatigue.

The Applicant has now found the regimen to administrate dronedarone to patients in a safe and effective way, those patients expecting to receive beta-blockers. Consequently, they found methods for managing the risk related to beta-blockers/dronedarone interaction. The methods according to the invention enable a method to decrease the risk of such an event, when dronedarone or pharmaceutically acceptable salts or esters thereof is administered for treating patients with paroxysmal or persistent atrial fibrillation (AF) or atrial flutter (AFL), with a recent episode of AF/AFL and associated cardiovascular risk factors (i.e., age >70, hypertension, diabetes, prior cerebrovascular accident, left atrial diameter ≥50 mm or left ventricular ejection fraction [LVEF] <40%), who are in sinus rhythm or who will be cardioverted.

The present invention relates to the use of dronedarone or pharmaceutically acceptable salts thereof in patients with paroxysmal or persistent atrial fibrillation (AF) or atrial flutter (AFL), with a recent episode of AF/AFL and associated cardiovascular risk factors (i.e., age >70, hypertension, diabetes, prior cerebrovascular accident, left atrial diameter ≥50 mm or left ventricular ejection fraction [LVEF] <40%), who are in sinus rhythm or who will be cardioverted to reduce the risk of cardiovascular hospitalization, said patients also expecting to receive a beta-blockers treatment, by performing the following steps a—initiate beta-blockers treatment at a low dose;
    b—performing electrocardiogram (ECG) verification of good tolerability;
    c—increase beta-blockers dose only if results in step b) are satisfying.

The present invention also relates to a method for managing the risk of dronedarone/beta-blockers interaction by using dronedarone or pharmaceutically acceptable salts thereof in patients with paroxysmal or persistent atrial fibrillation (AF) or atrial flutter (AFL), with a recent episode of AF/AFL and associated cardiovascular risk factors (i.e., age >70, hypertension, diabetes, prior cerebrovascular accident, left atrial diameter ≥50 mm or left ventricular ejection fraction [LVEF] <40%), who are in sinus rhythm or who will be cardioverted to reduce the risk of cardiovascular hospitalization, said patients also expecting to receive a beta-blockers treatment, by performing the following steps:

a—initiate beta-blockers treatment at a low dose;
    b—performing ECG verification of good tolerability;
    c—increase of beta-blockers dose only if results in step b) are satisfying.

In the instant invention, beta-blockers may be metoprolol or propranolol.

In some embodiments, dronedarone is administered 400 mg twice daily with meals.

In some embodiments a pharmaceutically acceptable salt of dronedarone is hydrochloride.

In step a), the term "low dose of beta-blockers" as used herein means a fraction of the recommended dose. In any case, this low dose is patient-dependent and may be defined taking into account individual patient's characteristics.

For example, a low dose may be
    for metoprolol, less than 200 mg e.g. as 100 mg;
    for propranolol, less than 160 mg, e.g. as 40 mg.

In step b), "ECG verification of good tolerability" and "ECG assessment" has the same meaning, i.e. assessments have to be made regarding for example heart rate, PR- and QTc-interval duration. For example heart rate may be higher than 50 bpm, PR-interval may be shorter than 200 ms.

In step c), increase or uptitration of beta-blockers will be a fraction of the recommended dose higher than the low dose as defined above up to a maximum dose of:
    200 mg for metoprolol,
    320 mg for propranolol.

The recommended dose is the dose defined in the labelling of the beta-blockers.

The maximum dose is defined according to the labelling of the beta-blockers.

The term "cardiovascular hospitalization" means a hospitalization which is caused by at least one of the following pathologies (Hohnloser et al., Journal of cardiovascular electrophysiology, January 2008, vol. 19, No. 1, pages 69-73):
relating to atherosclerosis,
myocardial infarction or unstable angina pectoris,
stable angina pectoris or atypical thoracic pain,
syncope,
transient ischemic event or cerebral stroke (except intracranial haemorrhage),
atrial fibrillation and other supraventricular rhythm disorders,
non-fatal cardiac arrest,
ventricular arrhythmia,
cardiovascular surgery, except heart transplant,
heart transplant,
implantation of a cardiac stimulator (pacemaker), of an implantable defibrillator ("ICD") or of another cardiac device,
percutaneous coronary, cerebrovascular or peripheral intervention,
variations in arterial pressure (hypotension, hypertension, except syncope),
cardiovascular infection,
major bleeding/haemorrhage (requiring two or more blood cell pellets or any intracranial haemorrhage),
pulmonary embolism or deep vein thrombosis,
worsening of congestive heart failure including acute pulmonary oedema or dyspnoea from cardiac causes.

Consequently, the prevention of cardiovascular hospitalization may be understood as the prevention of cardiovascular hospitalization for at least one of the above mentioned pathologies.

The present invention also relates to a method of providing dronedarone or pharmaceutically acceptable salts or esters, wherein said dronedarone or pharmaceutically acceptable salts or esters thereof is provided along with information indicating that it is useful for treating patients with paroxysmal or persistent atrial fibrillation (AF) or atrial flutter (AFL), with a recent episode of AF/AFL and associated cardiovascular risk factors (i.e., age >70, hypertension, diabetes, prior cerebrovascular accident, left atrial diameter ≥50 mm or left ventricular ejection fraction [LVEF] <40%), who are in sinus rhythm or who will be cardioverted to reduce the risk of cardiovascular hospitalization, and in case said patients also expecting to receive a beta-blockers treatment, the following steps should be observed:
 a—initiate beta-blockers treatment at a low dose;
 b—performing ECG verification of good tolerability;
 c—increase of beta-blockers dose only if results in step b) are satisfying.

In some embodiments, a pharmaceutically acceptable salt of dronedarone is hydrochloride.

In some embodiments, the information comprises printed matter that advises that dronedarone or pharmaceutically acceptable salts or esters thereof is useful for treating patients with paroxysmal or persistent atrial fibrillation (AF) or atrial flutter (AFL), with a recent episode of AF/AFL and associated cardiovascular risk factors (i.e., age >70, hypertension, diabetes, prior cerebrovascular accident, left atrial diameter ≥50 mm or left ventricular ejection fraction [LVEF] <40%), who are in sinus rhythm or who will be cardioverted to reduce the risk of cardiovascular hospitalization, and in case said patients also expecting to receive a beta-blockers treatment, the following steps should be observed:
 a—initiate beta-blockers treatment at a low dose;
 b—performing ECG verification of good tolerability;
 c—increase of beta-blockers dose only if results in step b) are satisfying.

The present invention also concerns a method of promoting the use of dronedarone or pharmaceutically acceptable salts or esters thereof, the method comprising the step of conveying to a recipient at least one message comprising dronedarone or pharmaceutically acceptable salts or esters thereof is useful for treating patients with paroxysmal or persistent atrial fibrillation (AF) or atrial flutter (AFL), with a recent episode of AF/AFL and associated cardiovascular risk factors (i.e., age >70, hypertension, diabetes, prior cerebrovascular accident, left atrial diameter ≥50 mm or left ventricular ejection fraction [LVEF] <40%), who are in sinus rhythm or who will be cardioverted to reduce the risk of cardiovascular hospitalization, and in case said patients also expecting to receive a beta-blockers treatment, the following steps should be observed:
 a. initiate beta-blockers treatment at a low dose;
 b. performing ECG verification of good tolerability;
 c. increase of beta-blockers dose only if results in step b) are satisfying.

In some embodiments a pharmaceutically acceptable salt of dronedarone is hydrochloride. The instant invention also concerns an article of manufacture comprising
 a) a packaging material;
 b) dronedarone or pharmaceutically acceptable salts or esters thereof or, and
 c) a label or package insert contained within the packaging material indicating that:
i) dronedarone or pharmaceutically acceptable salts or esters thereof is indicated in patients with paroxysmal or persistent atrial fibrillation (AF) or atrial flutter (AFL), with a recent episode of AF/AFL and associated cardiovascular risk factors (i.e., age >70, hypertension, diabetes, prior cerebrovascular accident, left atrial diameter ≥50 mm or left ventricular ejection fraction [LVEF] <40%), who are in sinus rhythm or who will be cardioverted to reduce the risk of cardiovascular hospitalization, and
ii) in case said patients also expecting to receive a beta-blockers treatment, the following steps should be observed:
 d. initiate beta-blockers treatment at a low dose;
 e. performing ECG verification of good tolerability;
 f. increase of beta-blockers dose only if results in step b) are satisfying.

In some embodiments a pharmaceutically acceptable salt of dronedarone is hydrochloride.

The invention also concerns a package comprising dronedarone or pharmaceutically acceptable salts or esters thereof and a label, said label comprising a printed statement which informs a prospective user that:
i) dronedarone or pharmaceutically acceptable salts or esters thereof is indicated in patients with paroxysmal or persistent atrial fibrillation (AF) or atrial flutter (AFL), with a recent episode of AF/AFL and associated cardiovascular risk factors (i.e., age >70, hypertension, diabetes, prior cerebrovascular accident, left atrial diameter ≥50 mm or left ventricular ejection fraction [LVEF] <40%), who are in sinus rhythm or who will be cardioverted to reduce the risk of cardiovascular hospitalization, and
ii) in case said patients also expecting to receive a beta-blockers treatment, the following steps should be observed:
 a. initiate beta-blockers treatment at a low dose;
 b. performing ECG verification of good tolerability;
 c. increase of beta-blockers dose only if results in step b) are satisfying.

In some embodiments a pharmaceutically acceptable salt of dronedarone is hydrochloride.

The invention also relates to a method for administering a combination of beta-blockers and dronedarone or a pharmaceutically acceptable salt thereof to a patient in need thereof, wherein said method comprises the following steps:
a. initiate beta-blockers treatment at a low dose;
b. performing ECG verification of good tolerability;
c. increase of beta-blockers dose only if results in step b) are satisfying.

In some embodiments a pharmaceutically acceptable salt of dronedarone is hydrochloride The term "pharmaceutically acceptable salts" as used herein means that the salts of the compounds of the present invention can be used in medicinal preparations. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, hydrobromic acid, sulfuric acid, methanesulfonic acid, 2-hydroxyethanesulfonic acid, p-toluenesulfonic acid, fumaric acid, maleic acid, hydroxymaleic acid, malic acid, ascorbic acid, succinic acid, glutaric acid, acetic acid, salicylic acid, cinnamic acid, 2-phenoxybenzoic acid, hydroxybenzoic acid, phenylacetic acid, benzoic acid, oxalic acid, citric acid, tartaric acid, glycolic acid, lactic acid, pyruvic acid, malonic acid, carbonic acid or phosphoric acid. The acid metal salts such as sodium monohydrogen orthophosphate and potassium hydrogen sulfate can also be formed. Also, the salts so formed may present either as mono- or di-acid salts and can exist substantially anhydrous or can be hydrated. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts, and salts formed with suitable organic ligands, e.g. quaternary ammonium salts.

It will also be specified that the expression "patients having a history of atrial fibrillation or atrial flutter", "patients with a history of or a current atrial fibrillation or flutter" or "patients with a recent history of or a current atrial fibrillation or flutter" or "patients with paroxysmal or persistent atrial fibrillation or flutter" or "patients with a history of, or a current paroxysmal or persistent atrial fibrillation or flutter" or "patients with a recent history of, or a current paroxysmal or persistent atrial fibrillation or flutter" or "patients with paroxysmal or intermittent atrial fibrillation or atrial flutter and a recent episode of atrial fibrillation or atrial flutter, who are in sinus rhythm or who will be cardioverted" or "patients with paroxysmal or persistent atrial fibrillation or atrial flutter and a recent episode of atrial fibrillation or atrial flutter, who are in sinus rhythm or who will be cardioverted" means a patient who, in the past, has presented one or more episodes of atrial fibrillation or flutter and/or who is suffering from atrial fibrillation or atrial flutter at the time the dronedarone or a pharmaceutically acceptable salt thereof is used. More particularly, this expression means patients with documentation of having been in both atrial fibrillation or flutter and sinus rhythm within the last 6 months preceding the start of treatment. Patients could be either in sinus rhythm, or in atrial fibrillation or flutter at the time the dronedarone or a pharmaceutically acceptable salt thereof is initiated.

The instant invention is further illustrated by the clinical data below.

EXAMPLE 1

This was a monocenter, randomized, double-blind, placebo-controlled, repeated dose, dose-escalating study in healthy male caucasian subjects, aged 25-40 years.

Subjects received metoprolol 200 mg OD alone for 5 days followed immediately by dronedarone 400 mg BID (Group 1), 600 mg BID (Group 2) or 800 mg BID (Group 3) and metoprolol 200 mg OD co-administration for 8 additional days. All treatments were administered in fed conditions. Blood samples were collected at trough before treatment and during the repeated administration, then over 12 h after the last dronedarone dose for dronedarone/SR35021 analysis, and up to 24 h after the last metoprolol dose for metoprolol/alpha-hydroxymetoprolol analysis.

Plasma dronedarone/SR35021 concentrations were determined using a validated liquid chromatography-mass spectrometry method, metoprolol and alpha-hydroxymetoprolol plasma concentrations were assessed using a validated High Performance Liquid Chromatography (HPLC) method with fluorescence detection.

Statistical Analysis

Pharmacokinetic parameters and before treatment concentrations on Day 5 and Day 13 were summarized using standard descriptive statistics. For dronedarone and SR35021, the dose effects were tested on Day 13 by ANOVA, using log transformed values. For metoprolol and alpha-hydroxymetoprolol, the dose effects were analyzed by ANOVA, using log transformed values and rank transformed values; if a group effect emerged, the Dunnet test was performed.

Day 13/Day 5 ratios, 90% and 95% CIs were also calculated.

Continuous demographic variables were summarized using standard descriptive statistics, qualitative variables summarized by count and percents.

The pharmacodynamic analyses were based on the change in Day 5 and Day 13 measurements, using a one-way analysis of variance (ANOVA) model with term for dose, for both primary and secondary endpoints; estimates and 95% confidence intervals (CI) of the difference in mean CHGDay13-5 between dronedarone dose groups and the placebo group were derived within the ANOVA framework. As the sample size calculation was based on the comparison of the highest dronedarone dose versus placebo, pairwise comparison were performed without adjustment of the overall treatment first type error rate. Safety evaluation was based upon a review of individual values and descriptive statistics (listings, summary tables, graphics).

Results

Mean (SD) values of pharmacokinetic parameters of metoprolol, alone and co-administered with dronedarone, and Day 5/Day 13 ratio estimates and confidence intervals are shown in table 1:

| Mean (SD) Parameters | Dronedarone/Placebo treatment | |
| --- | --- | --- |
| | Placebo (n = 11) | 800 mg/day (b.i.d) n = 4 |
| Metoprolol alone (day 5) | | |
| $C_{min}$ (ng/mL) | 30.3 (43.4) | 27.9 (17.5) |
| $C_{max}$ (ng/mL) | 100.6 (86.4) | 92.7 (39.8) |
| $t_{max}$ (h)* | 5.0 | 4.0 |
| $AUC_{0-24}$ (ng · h/mL) | 1541 (1563) | 1555 (803) |
| Metoprolol + dronedarone (day 13) | | |
| $C_{min}$ (ng/mL) | 36.3 (44.5) | 41.8 (26.6) |
| $C_{max}$ (ng/mL) | 134.1 (96.8) | 162.6 (55.5) |
| $t_{max}$ (h)* | 5.0 | 5.0 |
| $AUC_{0-24}$ (ng · h/mL) | 1862 (1689) | 2318 (846) |

-continued

| | Dronedarone/Placebo treatment | |
|---|---|---|
| Mean (SD) Parameters | Placebo (n = 11) | 800 mg/day (b.i.d) n = 4 |
| Ratio estimates (day 13/day 5) and 90% CI | | |
| $C_{max}$ (ng/mL) | 1.34 [1.08-1.66] | 1.84 [1.29-2.64] |
| $AUC_{0-24}$ (ng · h/mL) | 1.29 [1.08-1.55] | 1.63 [1.21-2.20] |

Whatever the administered dronedarone dose the metoprolol $C_{max}$ and $AUC_{0-24h}$ were significantly higher after 8 days of treatment.

As a function of the dronedarone administered dose, the effect tended to be higher:
1.8-fold increase in $C_{max}$
1.6-fold increase in $AUC_{0-24}$ There was a statistically significant reduction in Vcfmean (−0.28 s-1, p=0.0002), when dronedarone 800 mg BID was added on top of metoprolol 200 mg OD, indicating a reduction in myocardial contractility. Results on other contractility parameters using a different technique showed a similar trend.

Conclusion

Plasma metoprolol exposure at steady-state was increased by 1.6-fold after concomitant administration of therapeutic dose of dronedarone for 8 days.

At 400 mg BID, dronedarone increased steady-state metoprolol (200 mg OD) exposures by 1.6-fold, without significant effect on alpha hydroxymetoprolol exposures, in CYP2D6 extensive metabolizer subjects and is therefore a weak inhibitor of CYP2D6 in vivo. The interaction ratio is lower than the existing 3-($C_{max}$) to 6-fold (AUC) difference in metoprolol exposure between poor and extensive CYP2D6 metabolizers.

The above study is reported in Damy and al, Fundamental & Clinical Pharmacology, 18 (2004), 113-123 which is incorporated herein by reference.

EXAMPLE 2

This was a monocenter, open-label, non-placebo controlled study performed under Good Clinical Practice in healthy male subjects.

Subjects received dronedarone 800 mg OD alone, propranolol 80 mg OD alone, dronedarone and propranolol co-administration at same regimens described above for 7 days. All treatments were administered in fed conditions. Blood samples were collected at trough before and during the repeated administration, then over 12 h after the last dronedarone dose for dronedarone/SR35021 for dronedarone/SR35021 analysis, and up to 24 h after the last propranolol dose for propranolol analysis.

Plasma dronedarone/SR35021 concentrations were determined using a validated High Performance Liquid Chromatography (HPLC) with ultraviolet detection method, metoprolol plasma concentrations were assessed using a validated fluorimetric detection method.

Statistical Methods:

Pharmacokinetics: Propranolol, dronedarone and SR35021 $C_{bt}$ values were analyzed using repeated measures analysis of variance to assess "day" effects after repeated dosing. If a "day" effect was statistically significant, iterative analyses were performed without the earliest $C_{bt}$ until a non-significant effect was obtained; steady-state was assumed as soon as the "day" effect was non-significant. Propranolol $C_{bt}$ values after dosing with propranolol alone were compared to those obtained after dosing with dronedarone plus propranolol for "day", "treatment" and "day-by-treatment" effects. Propranolol $C_{max}$, $AUC_{0-12}$, and $AUC_{last}$ values were logarithmically transformed and analyzed for "treatment" effects of single and repeated dosing of propranolol versus dronedarone plus propranolol. dronedarone and SR35021 $C_{max}$ and $AUC_{0-24}$ values were analyzed to compare the "treatment" effect of a single dose of dronedarone with single dose of dronedarone plus propranolol. All $t_{max}$ values were analyzed using the non-parametric Wilcoxon's test.

Pharmacodynamics: Resting vital signs were summarized by the synthetic parameter $AUC_{0-8}$ and analyzed for "treatment effects and chronological ("time") effects using repeated measures analysis of variance. Exercise vital signs were analyzed in a similar manner; the electrocardiogram exercise data were not formally analyzed and presented using descriptive statistics.

Safety: Adverse events and laboratory parameters were summarized using descriptive statistics. Individual laboratory, vital sign and electrocardiogram parameters with values outside the reference range, or markedly changed during the study compared to baseline, were highlighted.

Results:

Pharmacokinetics

Trough levels ($C_{bt}$) of propranolol, dronedarone and SR35021 during repeated administration showed that steady-state conditions were obtained 24 hours after the first dose of propranolol and within the sixth day of administration for dronedarone. The mean (standard deviation) pharmacokinetic values are summarized below. There was no statistically significant "treatment" effect after single dosing. All propranolol parameters except $t_{max}$ showed statistically significant "treatment" effects after repeated dosing dronedarone plus propranolol compared to propranolol alone (table 2).

TABLE 2

| | Propranolol Alone | | dronedarone + Propranolol | |
|---|---|---|---|---|
| n = 16 Parameters (units) Propranolol | Single Dose Day 2 | Repeated Dose Day 8 | Single Dose Day 26 | Repeated Dose Day 32 |
| $C_{max}$ (ng/ml) | 59.79 (33.77) | 57.68 (31.47) | 68.65 (40.53) | 75.38 (42.05) |
| $T_{max}$ (h) | 2.19 (0.66) | 2.26 (0.57) | 2.06 (1.06) | 2.00 (0.89) |
| $AUC_{0-12}$ (ng · h/ml) | 318.75 (178.62) | 313.88 (175.01) | 359.14 (188.07) | 403.76 (234.77) |
| $AUC_{last}$ (ng · h/ml) | 360.85 (210.30) | 354.73 (214.63) | 403.30 (225.67) | 455.06 (284.21) |
| $R_{ac}$ | — | 1.00 (0.25) | — | 1.16 (0.20) |

TABLE 2-continued

| | | dronedarone Alone | dronedarone + Propranolol | |
|---|---|---|---|---|
| | n = 16 Parameters (units) | Single Dose Day 23 | Single Dose Day 26 | Repeated Dose Day 32 |
| dronedarone | $C_{max}$(ng/ml) | 140.5 (59.9) | 131.2 (58.3) | 219.9 (104.5) |
| | $t_{max}$ (h) | 3.63 (1.37) | 4.25 (1.39) | 4.06 (1.57) |
| | $AUC_{0-24}$ (ng · h/ml) | 983.1 (447.1) | 950.9 (419.3) | 1943.0 (1098.9) |
| SR35021 | $C_{max}$(ng/ml) | 85.9 (28.8) | 90.2 (32.8) | 111.3 (36.1) |
| | $t_{max}$ (h) | 5.13 (0.72) | 5.13 (1.20) | 4.94 (1.44) |
| | $AUC_{0-24}$ (ng · h/ml) | 768.6 (278.4) | 759.6 (284.7) | 1295.7 (510.7) |

Pharmacodynamics

Resting electrocardiogram heart rate fell compared to baseline after repeated once daily dosing of propranolol alone (−9%), and after coadministration of dronedarone and propranolol (−6%).

The PQ interval was lengthened after repeated once daily dosing of propranolol alone (4%), and after coadministration of the two drugs (12%). The QT interval was lengthened (4%) and the QTc interval was shortened (−2%) after repeated daily dosing of propranolol alone, but after coadministration of the two drugs there was slight lengthening of these interval (4% and 1%, respectively). The T-wave amplitude increased from baseline when propranolol was administered alone (28%). The increase was reduced when the two drugs were coadministered (8%). The changes from baseline in resting electrocardiogram parameters after single oral administration of propranolol or single oral coadministration of dronedarone and propranolol were similar to those seen after repeated dosing. Single oral administration of dronedarone alone induced an increase in the PQ interval, and an increase in the T-wave amplitude from baseline.

Resting heart rate, systolic blood pressure and diastolic blood pressure fell after repeated oral administration of propranolol alone (−8%, −5% and −10%, respectively) and after coadministration with dronedarone (−4%, −8% and −12%, respectively). There was a fall in all three parameters after a single dose of propranolol (−10%, −3% and −4%, respectively) and after coadministration of the two drugs (−5%, −7% and −7%, respectively). After the single dose of dronedarone there was an increase in heart rate (2%) and a fall in systolic blood pressure (−5%) and diastolic blood pressure (−3%).

During sub-maximal exercise there was a decrease in heart rate, systolic blood pressure and diastolic blood pressure from baseline after repeated oral administration of propranolol alone (−16%, −12% and −2%, respectively) and after coadministration with dronedarone (−21%, −18% and −7%, respectively). After a single dose propranolol there was a fall in heart rate (−17%) and systolic blood pressure (−13%), but a rise in diastolic blood pressure (2%). After single coadministration of the two drugs there was a fall in all three vital signs (−18%, −18% and −2%, respectively). There was also a fall from baseline after the single dose of dronedarone (−3%, −2% and −2%, respectively). None of the changes in electrocardiogram parameters or vital signs at rest or during sub-maximal exercise were considered to be clinically relevant. After repeated administration, the magnitude of the PR prolongation after the coadministration was 3 times greater than that observed for propranolol alone (11.9% versus 3.9%, p<0.001). The magnitude of the T-wave increase was statistically significantly lower during coadministration compared with propranolol alone (7.9% versus 28.3%, p=0.001). Based on AUC0-8 h, no difference in mean change from baseline in QT was observed between the coadministration and propranolol alone at steady state (4.4% versus 3.6%, respectively), but a statistically significant difference in mean change from baseline in QTc was observed (0.5% for coadministration versus −1.9% for propanolol alone, p<0.001), mainly linked to the reduction of HR in the dronedarone group (−6.4% versus −8.9% for propranolol). After the sub-maximal exercise test, no relevant changes in ECG parameters or vital signs were observed.

Conclusion

Repeated coadministration of 800 mg dronedarone and 80 mg propranolol significantly increased plasma concentrations of propranolol at steady-state (16% to 33%).

Single coadministration of 800 mg dronedarone and 80 mg propranolol did not modify the pharmacokinetic profile of either propranolol, dronedarone or SR35021. The pharmacodynamic effects of propranolol or dronedarone given alone were potentiated when the two compounds were coadministered.

Dronedarone (800 mg OD) slightly increased steady-state propranolol (80 mg OD) exposure by 1.2- to 1.3-fold, which can be explained by the inhibition of CYP2D6 by dronedarone.

Beta-blockers have been used in ATHENA clinical study according to the instant invention and at the same rate in the dronedarone group and in the placebo group. About 70 to 80% of the patients had received one of these compounds during the study. Table 3 shows the numbers and percentages of patients using beta-blockers except sotalol at the inclusion in the study, whereas table 4 shows the numbers and percentages of patients who received beta-blockers except sotalol as concomitant medications during the study.

TABLE 3

Number (%) baseline selected medications - All randomized patients

| | Placebo (N = 2327) | Dronedarone 400 mg BID (N = 2301) | Total (N = 4628) |
|---|---|---|---|
| beta-blockers except sotalol | 1641 (70.5%) | 1628 (70.8%) | 3269 (70.6%) |

TABLE 4

Number (%) of patients who received concomitant medications - All randomized patients

| | Placebo (N = 2327) | Dronedarone 400 mg BID (N = 2301) |
|---|---|---|
| beta-blockers except sotalol | 1860 (79.9%) | 1785 (77.6%) |

In the ATHENA trial, the object of the instant invention was used in the patients using both dronedarone and beta-blockers except sotalol. In those patients, there was no clinically significant increase of the risk of bradycardia and dronedarone has been shown to be effective for the prevention of mortality and morbidity (hospitalization) notably for the prevention of hospitalization for congestive heart failure or sudden cardiac death and the prevention of death due to stroke.

Results from ATHENA study are provided hereafter.

The relative risk (RR) was estimated using Cox's proportional-effect regression model.

The relative risk (RR) is the ratio of the rates of occurrence of a hospitalization or of a death among the patients on dronedarone, relative to the patients on placebo.

The percentage reduction x of a given event (hospitalization, death, cardiovascular death, etc.) is calculated in the following way:

$$x=1-\text{relative risk.}$$

Results Relating to the Prevention of Cardiovascular Hospitalization or Death

From the 4628 patients included in the trial, 2301 were part of the group treated with dronedarone hydrochloride.

1641 patients with beta-blockers baseline medication were part of the placebo group and 1628 patients with beta-blockers baseline medication were part of the group treated with dronedarone hydrochloride.

673 events were reported in the placebo group versus 553 in the group treated with dronedarone hydrochloride.

Calculated relative risk was equal to 0.777, i.e. a decrease of cardiovascular hospitalization or death of 23% in patients with beta-blockers baseline medication.

Results Relating to the Prevention of Death

From the 4628 patients included in the trial, 2301 were part of the group treated with dronedarone hydrochloride.

1641 patients with beta-blockers baseline medication were part of the placebo group and 1628 patients with beta-blockers baseline medication were part of the group treated with dronedarone hydrochloride.

673 events were reported in the placebo group versus 553 in the group treated with dronedarone hydrochloride.

Calculated relative risk was equal to 0.777, i.e. a decrease of death of 23% in patients with beta-blockers baseline medication.

Results Relating to the Prevention of Hospitalization for Congestive Heart Failure (CHF)

From the 4628 patients included in the trial, 2301 were part of the group treated with dronedarone hydrochloride.

1641 patients with beta-blockers baseline medication were part of the placebo group and 1628 patients with beta-blockers baseline medication were part of the group treated with dronedarone hydrochloride.

96 events were reported in the placebo group versus 85 in the group treated with dronedarone hydrochloride.

Calculated relative risk was equal to 0.888, i.e. a decrease of CHF of 12% in patients with beta-blockers baseline medication.

Results Relating to the Prevention of Hospitalization for Sudden Cardiac Death

From the 4628 patients included in the trial, 2301 were part of the group treated with dronedarone hydrochloride.

1641 patients with beta-blockers baseline medication were part of the placebo group and 1628 patients with beta-blockers baseline medication were part of the group treated with dronedarone hydrochloride.

25 events were reported in the placebo group versus 9 in the group treated with dronedarone hydrochloride.

Calculated relative risk was equal to 0.362, i.e. a decrease of sudden cardiac death of 64% in patients with beta-blockers baseline medication.

Results Relating to the Prevention of Death Due to Stroke

From the 4628 patients included in the trial, 2301 were part of the group treated with dronedarone hydrochloride.

1641 patients with beta-blockers baseline medication were part of the placebo group and 1628 patients with beta-blockers baseline medication were part of the group treated with dronedarone hydrochloride.

11 events were reported in the placebo group versus 10 in the group treated with dronedarone hydrochloride.

Calculated relative risk was equal to 0.909, i.e. a decrease of death due to stroke of 10% in patients with beta-blockers baseline medication.

What is claimed is:

1. A method for managing the risk of dronedarone/beta-blocker interaction in a patient with paroxysmal or persistent atrial fibrillation (AF) or atrial flutter (AFL), with a recent episode of AF/AFL and associated cardiovascular risk factors, who is in sinus rhythm or who will be cardioverted to reduce the risk of cardiovascular hospitalization, said patient also expecting to receive a beta-blocker treatment, comprising administering dronedarone or a pharmaceutically acceptable salt thereof to said patient, and then performing the following steps:
   a—initiating beta-blocker treatment in said patient at a low dose;
   b—and then performing a electrocardiogram (ECG) assessment in said patient; and
   c—then increasing beta-blocker dose to said patient only if results in step b) verify good tolerability.

2. The method according to claim 1, wherein dronedarone is administered 400 mg twice daily with meals.

3. The method according to claim 1, wherein the pharmaceutically acceptable salt of dronedarone is hydrochloride.

4. The method according to claim 1, wherein in step b), the beta-blocker dose may be increased up to a fraction of the recommended dose higher than the low dose.

5. The method according to claim 1, wherein the beta-blocker is metoprolol.

6. The method according to claim 5, wherein the low dose of metoprolol is less than 200 mg.

7. The method according to claim 5, wherein the low dose of metoprolol is 100 mg.

8. The method according to claim 1, wherein the beta-blocker is propranolol.

9. The method according to claim 8, wherein the low dose of propranolol is less than 160 mg.

10. The method according to claim 8, wherein the low dose of propranolol is 40 mg.

11. The method according to claim 1, wherein good tolerability is indicated by a heart rate higher than 50 bpm.

12. The method according to claim 1, wherein good tolerability is indicated by a PR-interval shorter than 200 ms.

13. The method according to claim 1, wherein the patient has at least one associated cardiovascular risk factor selected from the group consisting of:
   i. an age greater than 70;
   ii. hypertension;
   iii. diabetes;
   iv. a prior cerebrovascular accident,
   v. a left atrial diameter greater than or equal to 50 mm; and
   vi. a left ventricular ejection fraction less than 40%.

14. The method according to claim 13, wherein the patient has hypertension.

15. The method according to claim 13, wherein the patient has diabetes.

16. The method according to claim 1, wherein the patient had an episode of atrial fibrillation or atrial flutter with the last 6 months.

* * * * *